United States Patent [19]

Renirie

[11] 4,097,766
[45] Jun. 27, 1978

[54] LOW CURRENT DRAIN AMPLIFIER SYSTEM

[75] Inventor: Alexis C. M. Renirie, Nijmegan, Netherlands

[73] Assignee: Vitatron Medical B.V., Dieren, Netherlands

[21] Appl. No.: 738,585

[22] Filed: Nov. 3, 1976

Related U.S. Application Data

[62] Division of Ser. No. 608,465, Aug. 28, 1975, Pat. No. 4,043,347.

[51] Int. Cl.² ............................................. H03K 17/00
[52] U.S. Cl. ................................... 307/229; 307/230; 307/361; 328/146
[58] Field of Search ..................... 307/229, 230, 361; 330/30, 69; 328/146–147

[56] References Cited

U.S. PATENT DOCUMENTS

| | | | |
|---|---|---|---|
| 3,989,958 | 11/1976 | Renirie et al. | 307/230 |
| 3,989,959 | 11/1976 | Renirie et al. | 307/230 |
| 4,023,046 | 5/1977 | Renirie et al. | 307/230 |

Primary Examiner—Stanley D. Miller, Jr.
Assistant Examiner—B. P. Davis
Attorney, Agent, or Firm—Woodcock, Washburn, Kurtz & Mackiewicz

[57] ABSTRACT

A low current drain amplifier system, adaptable for use in cardiac pacers and other applications requiring low current drain operation, having an amplifier path comprising transconductance amplifier means characterized by having the circuit characteristic of a current source at its output, the transconductance amplifier means direct driving an active circuit having a high impedance input, and a current source supply for maintaining fixed current operation of the amplifier system elements. In the preferred embodiment, the amplifier path contains a first OTA operating as an amplifier of received signals, the first OTA having its output direct coupled to an input of a second OTA which operates as a comparator, the output of the comparator OTA being direct connected to an IC transistor element.

21 Claims, 4 Drawing Figures

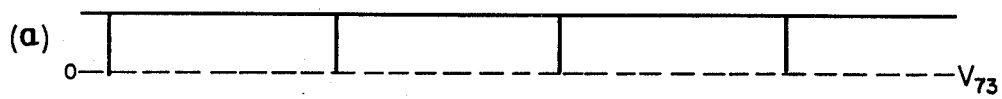
(a) $V_{73}$
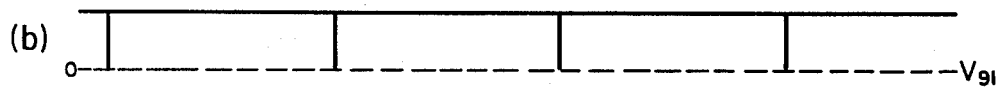
(b) $V_{91}$
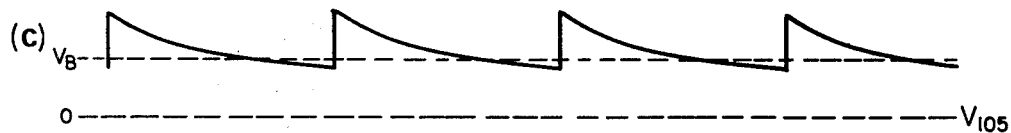
(c) $V_B$ — $V_{105}$
(d) $V_{74Be}$
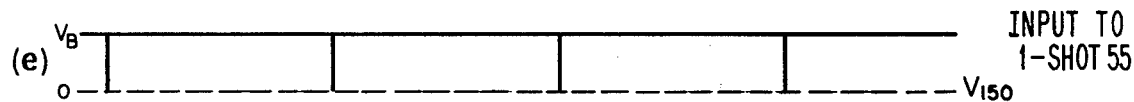
(e) $V_B$ INPUT TO 1-SHOT 55 — $V_{150}$
(f) $V_B$ INPUT TO FF1 $Cl_1$ (FLIP FLOP 56)
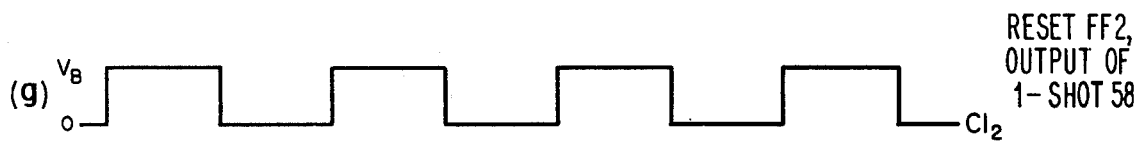
(g) $V_B$ RESET FF2, OUTPUT OF 1-SHOT 58 $Cl_2$
(h) $FF_1$
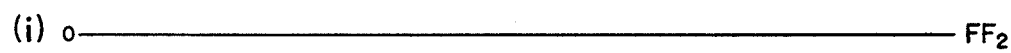
(i) $FF_2$
Fig. 3

LOW CURRENT DRAIN AMPLIFIER SYSTEM

This is a division, of application Ser. No. 608,465, filed Aug. 28, 1975, now U.S. Pat. No. 4,043,347, 8/23/77.

BACKGROUND OF THE INVENTION

1. Field of the Invention

This invention lies in the field of amplifier systems and, more particularly, low current drain amplifier systems adapted for low power operation such as in cardiac pacing devices.

2. Description of the Prior Art

Cardiac pacers are, by this time, widely known and utilized by those skilled in the art. There is a widespread use of implanted pacers, as well as temporary pacers as used in cardiac care units. While the general success of cardiac pacers as such has been demonstrated by their adoption by cardiologists and physicians, there remains a pressing need for improvement of cardiac pacers, both in terms of the functions that the pacers are able to perform and the efficiency and reliability of such performance. As expected, when the sophistication of various functions performed by the pacer is increased, there is a concomitant increase in the required circuit complexity and correspondingly a decrease in reliability and efficiency. The fundamental need in the art is to provide a reliable pacer which incorporates the desired pacer functions in an efficient manner while optimizing usage of the power source and providing an integrity of operation which is substantially independent of the condition of the power source and other operating variables.

An essential need in the field of cardiac pacers, as well as other applications where low level signals must be amplified and processed very efficiently, is to provide amplifier circuitry having a low current drain, and which is designed to provide extreme reliability in terms of maintaining desired signal sensitivity and being continuously operative independent of power source variations. In particular, in the field of cardiac pacers it is desirable to provide amplifier and logic circuitry having a total average current drain on the order of about 1 microamp, without sacrificing the desired circuit characteristics. For operation in a demand type cardiac pacer, the requirement is that the amplifying system provide amplification of the detected low level signals which emanate from the heart, and further provide transformation of such analog signals into digital signals suitable for processing in the logic portion of the pacer. There is thus a required low current operation circuitry which is substantially independent of the power source condition and which effectively provides a high speed, high gain operation.

SUMMARY OF THE INVENTION

It is an object of this invention to provide an amplifier system adaptable for operation as part of a signal processing system, and which operates at a minimum power level and is susceptible of easy and accurate adjustment to provide desired operating characteristics.

It is another object of this invention to provide amplifier circuitry adaptable for use in a cardiac pacer, or like environment, and which operates with a predetermined input signal sensitivity, which sensitivity is effectively independent of pacer operating conditions, and which operates with a minimum current drain.

In accordance with the above objectives, there is provided pacer apparatus comprising first amplifier means for amplifying a received input signal, which amplifier means is characterized by having an output circuit characteristic of a current source, a comparator which is direct driven by the amplifier means, the comparator also having an output characteristic of a current source, the amplifier means and comparator cooperating to provide an output of a predetermined sensitivity. The output of the comparator is direct coupled to a high input impedance active device, such as an IC transistor element, the total combination providing an effective high gain signal detecting path. Circuit sensitivity and overall current drain of the circuit are controlled by current source circuitry which supplies required power for all of the elements of the amplifier system.

BRIEF DESCRIPTION OF THE DRAWINGS

FIG. 3 is a series of curves illustrating performance of the pacer when no natural beats, or R waves, are detected.

DESCRIPTION OF THE PREFERRED EMBODIMENT

Figure 1:
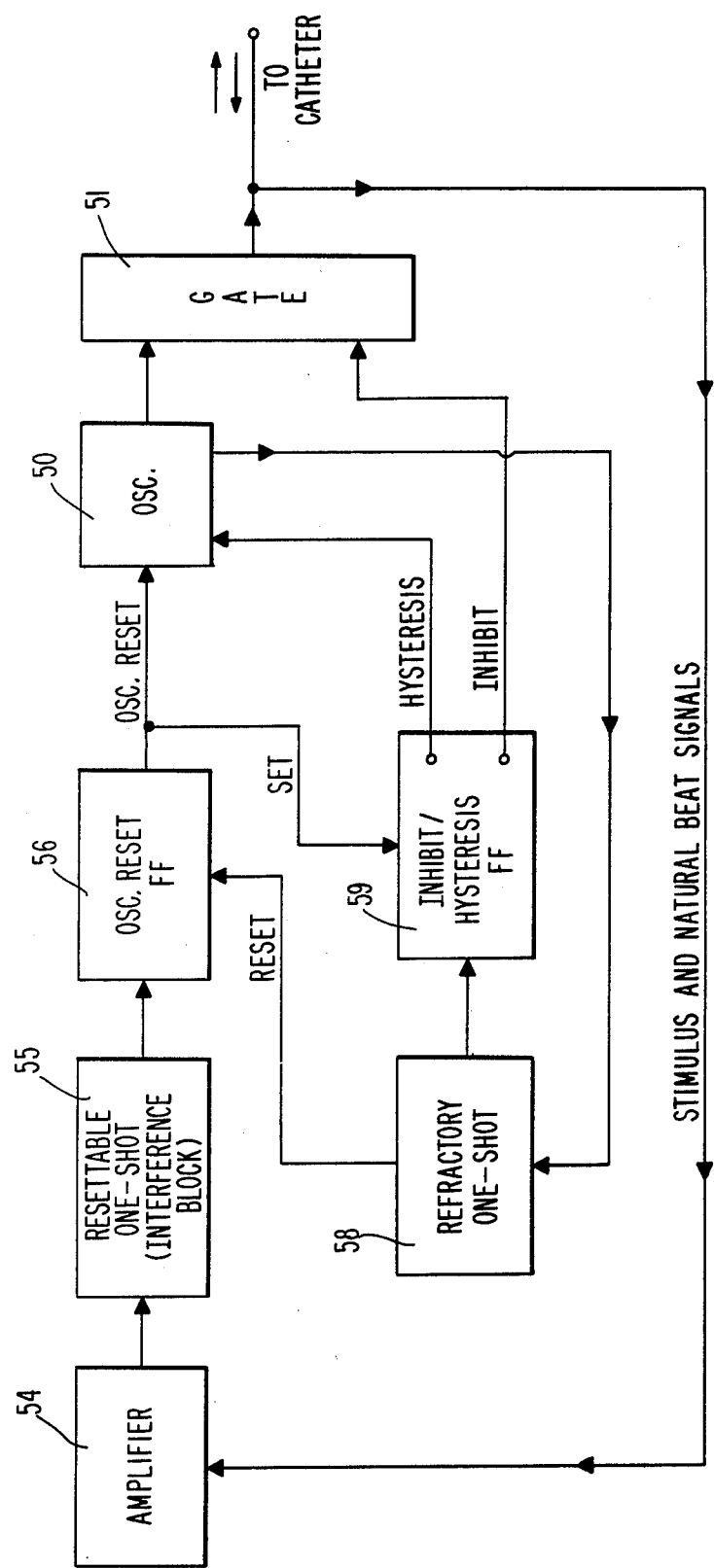
FIG. 1 is a block diagram illustrating the functional components of the pacer apparatus of this invention.
Figure 2:
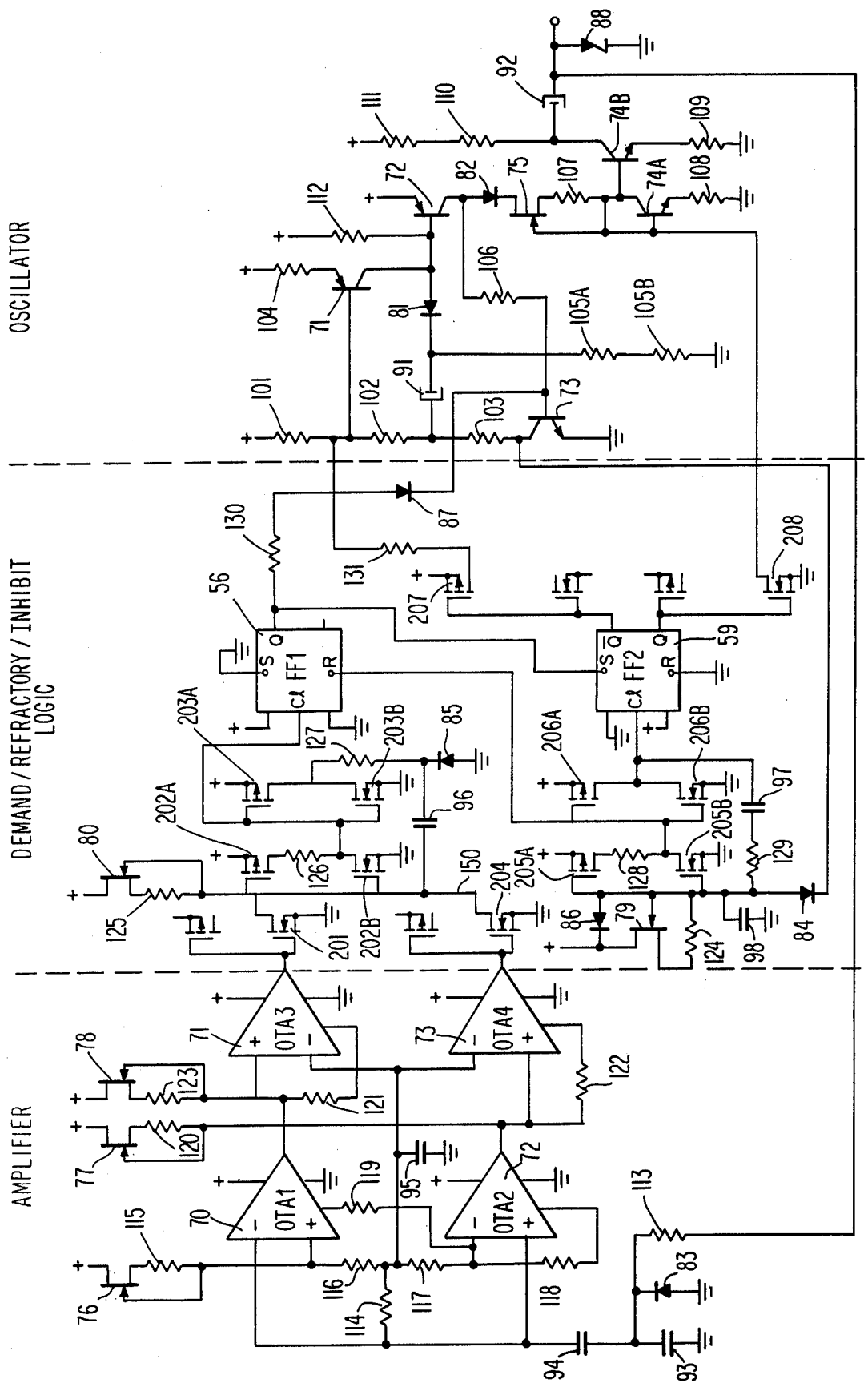
FIG. 2 is a circuit diagram of the pacer of this invention.

Referring now to FIG. 1, the overall operation of the pacer of this invention can be seen by examination of the functional blocks. The central element of the pacer is an oscillator 50, which is suitably designed to run at a fixed rate when not inhibited. The output signals or pulses of oscillator 50, adapted in shape and strength for stimulation of the patient's heart, are connected to a gate 51, which normally passes the pulses through to the catheter device which physically transmits the cardiac signals and delivers them at the desired location within the heart. As shown to the right of block 51, the catheter, or other transmission means, both transmits generated stimulus signals to the heart and picks up natural heartbeats and delivers them to the pacer unit. Both delivered stimulus signals and received natural heartbeat signals are connected to an amplifier 54, which in this embodiment incorporates means for providing output signals only when the delivered input signals exceed a predetermined threshold level. The design criterion at this point is to amplify, to a strength suitable for further processing, signals corresponding to the expected strength of the physiological signals that are being monitored. Specifically, in the demand pacer case, the amplifier must detect and amplify QRS waves generated within the cavity of the ventricle. Thus, the threshold characteristic of amplifier 54 may be set to amplify positive or negative going signals of a magnitude exceeding the smallest expected QRS wave. It is to be noted, however, that the amplifier as presented in the preferred embodiment of this invention, as seen in FIG. 2, may be adapted for detection of signals comprising a wide range of magnitudes and frequencies, and the amplifier as such is not limited in its frequency response characteristics. In the pacer application, the amplifier bandwidth is set at one kHz.

The output of amplifier 54 is connected to a continuously settable one shot circuit, also referred to as a monostable multivibrator, designated as 55. This one shot circuit performs the dual functions of generating a signal appropriate for triggering the following circuit, which is oscillator reset flip-flop 56, and also providing an interference block whereby transmission to flip-flop 56 is prevented as long as successive signals appear at the output of amplifier 54 separated in time by a period less than a predetermined interference interval. Thus, one shot 55 is the central logic component for carrying out the desired interference blocking function, and also is part of the circuit path for generating the required signal for resetting oscillator 50 upon detection of a natural heart signal.

Oscillator reset flip-flop 56, in the preferred embodiment, changes its state upon receipt of an upswinging signal from one shot 55, in the absence of a reset signal at its reset terminal. When flip-flop 56 is triggered, an enabling signal from its output is connected to oscillator 50 so as to reset its timing, whereupon oscillator 50 is effectively set at the beginning of its timing cycle and generation of a stimulus signal is inhibited for a time period corresponding to the pacer escape interval. The pacer escape interval is, of course, determined by the time-out period of the oscillator. The output from flip-flop 56 is also connected to a second flip-flop 59, which is characterized as an inhibit/hysteresis flip-flop. This signal is connected to the set input of this latter flip-flop, thus setting it. Oscillator 50, at the time that it is either reset or times out and delivers a stimulus signal, produces an output which is connected to a second one shot circuit 58, designated a refractory one shot. One shot 58 is a monostable multivibrator of the same general form as circuit 55, and is triggered to its unstable state upon the occurrence of either a generated stimulus pulse or the resetting of oscillator 50. Upon being triggered into its high or unstable state, circuit 58 delivers a reset signal which is connected to the reset terminal of flip-flop 56, and also delivers a trigger signal to flip-flop 59. Circuit 58 is configured to stay in its own stable state for a time period corresponding to the desired refractory period, such that flip-flop 56 is reset and consequently disenabled from reacting to an input clock pulse, for a time period corresponding to the refractory period. The output from one shot 58 is also connected to flip-flop 59, which flip-flop is triggered when and only when there is a set signal on its set terminal, i.e., only after setting of flip-flop 56. This flip-flop is triggered by the change of level of the output from one shot 58, and stays in a changed state for a time period identical to the time period set by one shot 58. When in its changed state, flip-flop 59 provides an inhibit signal to gate 51, thereby preventing transmission of any stimulus signal through to the catheter at the time the oscillator is reset. It is to be noted, however, that no inhibit signal is generated when the oscillator times out because no set signal has been connected to flip-flop 59. At the same time that the inhibit signal is generated and only when the inhibit signal is generated, a hysteresis circuit associated with oscillator 50 is enabled, whereby the oscillator escape interval is adjusted corresponding to a lower rate so long as natural signals are detected.

Reference is now made to FIG. 2 for a discussion of the detailed circuit diagram of the pacer of this invention. Referring first to the oscillator, the timing is centered around the charging of capacitor 91 and the action of transistors 72 and 73. Transistors 72 and 73 are alternately either both conducting or both not conducting. The emitter of transistor 72 is connected to plus voltage, and the base is connected through diode 81 to one terminal of capacitor 91, the other capacitor terminal being connected jointly to resistors 102 and 103. Resistor 102 is connected through resistor 101 to plus voltage, and also to the base of transistor 71, the collector of which is connected to the base of transistor 72 and emitter of which is connected through resistor 104 to the plus voltage supply. Resistor 103 is further connected to the collector of transistor 73, the emitter of which is connected to ground and the base of the base of which is connected through resistor 106 to the collector of transistor 72. Resistors 105A and 105B form an adjustable resistor pair, the value of which is established according to the desired pulse interval time period, these resistors being connected between capacitor 91 and ground. The collector of transistor 72 is connected through diode 82 to a gate formed by transistors 75 and 74A, and resistors 107 and 108. The collector of transistor 74A is connected to the base of transistor 74B, and the collector of transistor 74B is connected through resistors 110 and 111 to the positive supply, as well as through output capacitor 92 to the pacer output terminal. The output terminal is connected to system ground through zener diode 88.

In operation, between output pulses transistors 72 and 73 are in an off, or non-conducting condition, and capacitor 91 is discharging through the combined resistive path formed by resistors 101, 102, 105A and 105B. Resistors 105A and 105B are generally of much greater magnitude than resistors 101 and 102, such that the time constant is appreciably the value of capacitor 91 times the combined resistance of 105A and 105B. As capacitor 91 charges through this path to the point where the voltage at the cathode of diode 81 is just less than the positive supply voltage, $V_B$, diode 81 and transistor 72 are turned on. Turning on of transistor 72 provides a current path from the positive supply through resistor 106 to the base of transistor 73, whereby the latter transistor is also turned on. With both transistors 72 and 73 in an on state, a charging path for charging of capacitor 91 is created through diode 81, resistor 103 and transistor 73, which path has an approximate time constant determined by resistor 103, which may be of the order of 6K, and capacitor 91. Charging takes place as long as the current through capacitor 91 sustains saturation of transistor 72, but as capacitor 91 becomes charged to substantially $V_B$, transistor 72 turns off, thereby turning off transistor 73. At this time, the timing out of the circuit recommences with the discharging of capacitor 91 through resistors 101 and 102, until the two transistors are again triggered into conduction. It is noted that these transistors can also be triggered into conduction by transmission of a positive signal through diode 87 to the base of transistor 73, which turns that transistor on, thereby forward biasing transistor 72 and also driving it to conduction.

When capacitor 91 is charging through diode 81, the time interval of the output pulse would normally be a function of the exponential charging characteristic determined by the value of capacitor 91 and resistor 103. However, during this charging, the voltage across resistor 101 increases, and when the voltage on the base of transistor 71 drops by an amount corresponding to the forward base-emitter bias voltage of that transistor, the transistor is turned on. In its on state, transistor 71 cuts off the base current of transistor 72, thereby turning off transistors 72 and 73. This enables more accurate control of the time interval of the output pulse, since the controlled current flow through transistor 71 enables limiting of the charging time and thus a limiting of the time until transistors 72 and 73 are turned off, at which time the output pulse is terminated.

When transistor 72 conducts, an output signal is transmitted through transistor 75 to the base of transistor 74B, driving it to conduction, whereupon there appears at the collector of transistor 74B a negative going signal which is connected through output capacitor 92 to the catheter. However, note that the base of transistor 74A and the gate of FET 75 are connected to the drain of CMOS transistor 208, which is shown in the logic section. As long as 208 is not conducting, transistors 74A and 75 will conduct, but if CMOS transistor 208 is driven to conduction, transistors 74A and 75 are taken out of conduction, thereby inhibiting or preventing transmission of a generated stimulus pulse through transistor 74B and capacitor 92.

Referring now to the amplifier portion of the apparatus, it is seen that input signals are transmitted through resistor 113 and capacitor 94 to amplifiers 70 and 72 respectively, which are also designated as OTA 1 and OTA 2. Diode 83, connected between capacitor 94 and ground serves to clip incoming signals, such as is the case with delivered stimulus signals, to limit the size of the inputs to the amplifier. Capacitor 93 acts to filter incoming unwanted high frequency signals. The input signal connected through capacitor 94 is, in the embodiment shown, inputted to a two path amplifier comprised of amplifier pairs 70-71 and 72-73. These amplifiers, referred to as OTA 1-4, are operational transconductance amplifiers, such as the model CA3080 made by RCA. Reference is made to the available literature published by the manufacturer for the operating characteristics of these amplifiers. It is sufficient for this disclosure to point out that these amplifier units are characterized by high input impedances, a transconductance which is a function of the current input into one of its terminals, and an output current which is equal to the transconductance times the difference of the two inputs to the amplifier. At its output, each OTA acts as a current source, and the output current is a function of the difference of the two applied input signals. By applying a bias, or reference voltage to one of the two differential input terminals of the OTA, the OTA can be utilized as a comparator, such that when the input differential voltage changes from one polarity to the other, the output is switched, which is a useful characteristic for high speed pulse generation. The total current drain of each OTA, including the bias current, is approximately three times the bias current, such that drain can be maintained at an extremely low level by maintaining the bias current at a low level. In practice, current drains of appreciably less than 1 microamp are achieved for these amplifiers.

The input signal to OTA 1 is connected to the negative, or inverting terminal, whereas the same input is connected to the positive or non-inverting terminal of OTA 2. The respective other input terminals of OTA 1 and OTA 2 are provided from the positive power supply through the current source established by FET 76 and resistor 115. The output of this current source is connected first to the positive terminal of OTA 1, and then through the resistive combination of resistors 116 and 117 to the negative terminal of OTA 2. The negative terminal of OTA 2 is also connected through resistor 119 to the bias current input of OTA 1, and through resistor 118 to the bias current input terminal of OTA 2, thereby establishing the transconductance values of the two OTAs. Since the input impedances at the voltage input terminals are high, the bias currents are appreciably set by the current source and by the bias resistors 118 and 119 respectively. The junction between resistors 116 and 117 is connected to the input terminals through resistor 114, and is also connected to the negative, or inverting input terminals of OTA 3 and OTA 4, thereby providing a comparator, or reference voltage for each of these OTAs. Capacitor 95 is connected between resistor 114 and ground, to decouple the junction 116/117.

Additional current sources are provided by the combinations of FET 77 and resistor 120, which is connected to the output of OTA 2, and the FET 78 and resistor 123, which is connected to the output of OTA 1. The output currents of the first two OTAs, which provide amplification, are each connected to the positive, or non-inverting input terminal of a respective one of the second two OTAs. The second OTAs are also bias current controlled from their respective current sources through resistors 121 and 122 respectively. In this arrangement, the output of each of the first amplifiers is coupled into a current source in parallel with a resistor, i.e., resistors 121 and 122 respectively, giving a voltage gain in the range of 10 to 20. The amplified signal is then compared with a predetermined bias, or threshold voltage, at the input to the next amplifier, such that the second amplifier provides an output signal only when the input exceeds a predetermined value, thereby providing a threshold function. In this arrangement, amplifiers OTA 1 and OTA 3 handle negative going signals, and amplifiers OTA 2 and OTA 4 handle positive going signals, the two amplifier pairs suitably being adjusted symmetrically so that each has the same absolute magnitude threshold.

Referring now to the logic circuit, it is seen that this portion of the pacer contains a plurality of integrated circuits. The integrated circuits utilized in the preferred embodiment are "CMOS" devices, meaning complementary metal oxide semiconductors. In particular, the invention as reduced to practice incorporates the model CD4007A dual complementary pair plus inverter. Information on the characteristics and use of this integrated circuit (IC) device is found in the literature, for example, the RCA Solid State Data Book series, 1973 edition on COS/MOS Digital Integrated Circuits. In the circuit diagram of FIG. 2, a plurality of the complementary pairs are shown, and in several instances only one of the two units in the pair is utilized, such that it acts effectively as a single enhancement type field effect transistor. In describing the separate units of each pair, as they are shown schematically, they will be described as separate transistors, although it is appreciated that the embodiment shown incorporates chips which include three complementary pairs. Of course, single MOS/FET or other devices could also be utilized.

The output of OTA 3 is connected to the gate of transistor 201, the drain of which is connected to line 150 which is connected to the positive power source through a current source composed of FET 80 and resistor 125. Likewise, the output of OTA 4 is connected to the gate of transistor 204, the drain of which is also connected to line 150. It is thus seen that each of the OTA outputs drives into the high impedance gate input of an IC, either transistor 201 or 204, which IC is in turn outputted into a current source. This combination provides for an extremely high voltage gain operation. Further, the arrangement permits turning on of the IC without causing significant current drain, since the IC is outputted into a current source which holds current to a predetermined limit. The connection between OTA 4 and transistor 204 and the current source comprised of transistor 80 and resistor 125 is the same, such that the same operating characteristics are obtained when a signal comes through OTA 4.

The output of the IC, at line 150, is connected to monostable flip-flop 55 (FIG. 1) which comprises transistors 202A, 202B, 203A, and 203B, in combination with the feedback path comprised of resistor 127 and capacitor 96. Diode 85 is connected between capacitor 96 and ground, to provide one way current flow with respect to the capacitor. This arrangement provides a resettable type monostable flip-flop, with the time period in which the circuit stays in the unstable state being determined by current source 80 and capacitor 96. The monostable one shot is triggered when the input at line 150 drops to the zero state, or ground, which occurs when there is an output from either OTA 3 or OTA 4, as seen in curve (e) of FIG. 3. Line 150 is normally maintained at about the power supply level $V_B$, since transistors 201 and 204 are both nonconducting, but as soon as either one is driven to the conductive state, line 150 is effectively grounded, thus triggering the one shot.

The output from the one shot is taken from the output of transistors 202A and 202B which is connected to the common gates of transistors 203A and 203B, connected to the clock input terminal of flip-flop 56. Flip-flop 56 is a JK type flip-flop, which is a commercially available item. The clock input terminal responds only to voltage edges, and the set and reset inputs respond only to voltage levels. As indicated in FIG. 2, flip-flop 56 is normally set, such that it is triggered by the rising slope of a clock pulse, but when it is reset by a signal at the reset terminal, it is insensitive to an incoming clock pulse. The output of flip-flop 56, taken at the Q terminal, is connected through resistor 130 and diode 87 to the base of transistor 73, for the purpose of resetting the oscillator 50.

The refractory one shot 58 which is also a monostable multivibrator, is comprised of CMOS transistors 205A, 205B, 206A and 206B, in combination with resistor 128, resistor 129 and capacitor 97. The input to this one shot is delivered from the collector of transistor 73 through diode 84 to the common gate of transistors 205A and 205B. Capacitor 98 couples this point to ground. The common gate is also connected to the positive voltage source through an effective current source provided by FET 79 and resistor 125. Diode 86 gives a current path for the discharging current of capacitor 97 after returning to steady state; in spite of the fact that this current is limited by resistor 129 and could also flow through the protection diodes of the CMOS and the gate-channel diode of junction FET 79, diode 86 prevents any superfluous current through these low leakage and therefore high threshold diodes. An output of refractory one shot 58 is taken from the outputs of transistors 205A and 205B connected to the common gate of transistors 206A and 206B, and connected to the reset terminal of flip-flop 56. In the normal state, when the oscillator is timing out, transistor 73 is non-conducting such that diode 84 is non-conducting, holding a high input at the common gate of transistors 205A and 205B, whereby transistor 205B is in the conducting state, holding a zero or low signal on the reset terminal of flip-flop 56. When the oscillator times out, or is reset, transistor 73 is driven into saturation, placing a negative going signal onto the common gate of transistors 205A and 205B, thereby driving transistor 205A into conduction and triggering the one shot, whereby a high signal is placed on the reset terminal of flip-flop 56. When this happens, a clock pulse is received at flip-flop 59. Flip-flop 59 is set when flip-flop 56 is set, i.e., after a heartbeat, and reset when one-shot 58 returns to its steady state at the end of the refractory period. At the end of the refractory period, the clock signal into flip-flop 59 is positive-going (the inverse of the $Cl_2$ signal illustrated in FIGS. 3 and 4), and resets flip-flop 59. As long as flip-flop 59 is "on", i.e., during the refractory period caused by the heartbeat, its Q output is high, driving transistor 208 to conduction and turning off transistor 74A, thereby inhibiting the output gate.

The Q output terminal of flip-flop 59 is connected to the gate of transistor 207, the drain of which is connected through resistor 131 to the connection between resistors 101 and 102. The $\overline{Q}$ output is normally high, holding transistor 207 off, thereby blocking current flow through resistor 131. However, when heartbeats are sensed, such that the oscillator is reset, and flip-flop 59 is set, $\overline{Q}$ goes to zero, thereby turning on transistor 207 and creating a current path through resistor 131 which shunts resistor 101. In this condition, the voltage on capacitor 91 must go to a higher value before transistor 71 can be turned on to finish charging the capacitor. Thus, capacitor 91 charges to a higher voltage than normal, resulting in a longer discharging period. Thus, the combination of flip-flop 59, transistor 207, resistor 131 and the oscillator 50 operate to provide hysteresis to the pacer, whereby the time out, or escape interval is lengthened whenever the patient's natural heartbeat is present.

Figure 4:
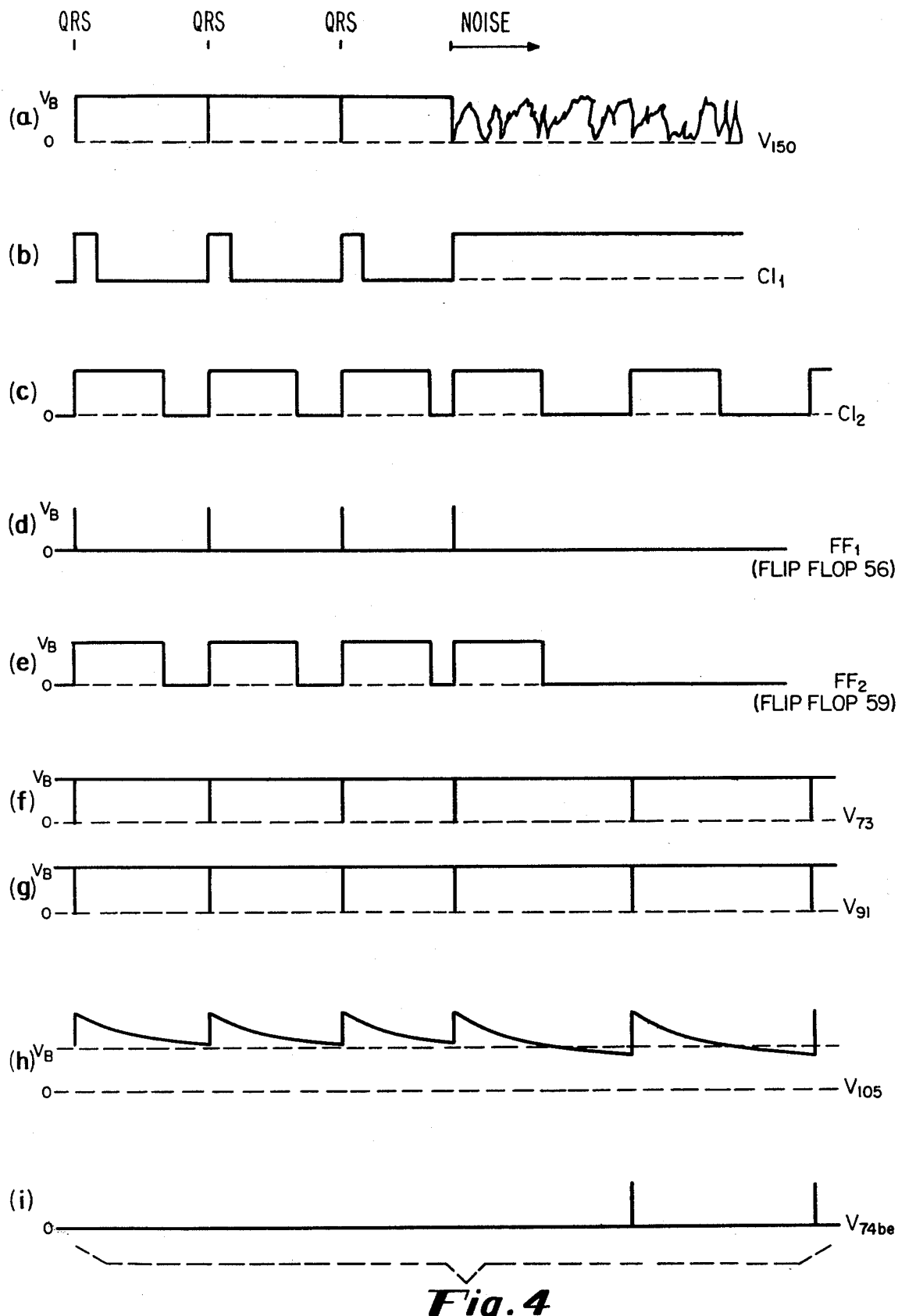
FIG. 4 is a series of curves illustrating performance of the pacer when natural beats are detected, and also when noise signals are present.

Reference is now made to FIGS. 3 and 4, in conjunction with which the overall operation of the pacer under different conditions is examined. FIG. 3 shows curves illustrating a number of circuit conditions as a function of time, in the situation where no QRS waves are detected, i.e., the pacer is operating in a free running mode at a fixed frequency. Curves (a), (b) and (c) represent the voltage at the collector of transistor 73, at the junction between capacitor 91 and resistors 102 and 103, and across resistors 105A and 105B respectively. As is seen, when the oscillator times out, transistor 73 is driven into a conducting state, placing its collector substantially at ground. Since resistor 103 is small compared to the combination of resistors 102 and 101, $V_{91}$ also drops substantially to ground at the point of oscillator triggering. Corresponding to switching of transistor 73, transistor 74B is also driven to conduction, which is shown in curve (d) where the emitter voltage (74Be) is plotted. The negative going output stimulus, which is generated at the collector of transistor 74B and transmitted through capacitor 92, is inputted to the amplifier section, producing a low signal at line 150, as shown in curve (e). As discussed above, when this input to one shot 55 appears, the one shot produces a clock output pulse, as shown in curve (f), which is inputted to flip-flop 56. At the same time, the negative going signal from transistor 73 is inputted to refractory one shot 58, which produces an output signal designated $Cl_2$ as shown in curve (g), which is connected to the reset terminal of flip-flop 56. The clock signal for flip-flop 59 (FF2) is the inverse of this $Cl_2$ signal. Although not shown in curves (f) and (g), the timing is such that the leading edge of the Cl₂ pulse precedes the leading edge of the Cl₁ pulse, such that flip-flop 56 is reset before it can be triggered by the Cl₁ pulse. Accordingly, there is no response at the Q output of flip-flop 56 as seen in curve (h). For this reason, flip-flop 59 is not set, such that it is not responsive to the positive edge of the clock signal it receives, and produces no output at its Q terminal, as shown in curve (i).

Referring now to FIG. 4, conditions are illustrated where first QRS signals are present, and then noise, or interference is picked up, as illustrated in curve (a). The amplified signals shown in curve (a) are inputted to resettable one shot 55, which produces the clock pulses shown in curve (b). These clock pulses trigger FF1, producing outputs at the Q terminal as shown in curve (d). These outputs are connected to the base of transistor 73, causing it to be driven to conduction, thereby resetting the oscillator. At the same time, a signal is transmitted to the set terminal of FF2, triggering it to the set state. The resetting of the oscillator causes triggering of one shot 58, which times out the refractory period, dafter which FF2 is reset. The output of FF2, shown in curve (e), produces an inhibit signal at gate 51, which inhibits transmission of the oscillator signal through to the catheter. The time delay between transmission of the reset signal to the oscillator and transmission of the inhibit signal to gate 51 is small enough so that the stimulus signal produced by oscillator 50 is fully blocked. Note also that the Cl₂ pulse is delayed slightly behind the Cl₁ pulse, such that FF1 is first triggered and then reset.

When noise appears at the output of the amplifier, the output of the resettable one shot 55 remains at a high level, due to the fact that this one shot is continually set, or set again, by the voltage level of the amplifier output. Consequently, if a repeated signal comes through from the amplifier before the one shot has timed out, it is set again, and the capacitor 96 must time out through the full time interval before the one shot returns to its stable state. Thus, by setting the timing of the one shot through capacitor 96 and current source 80, desired interference selection can be made.

It is to be noted that there are four communication paths between the logic circuitry and the oscillator. The oscillator reset signal is communicated from FF1 to transistor 73, for purposes of resetting the timing of the oscillator following the detection of a natural signal. A refractory signal is transmitted from the oscillator to the refractory one shot circuit following both delivered stimulus pulses and resetting due to detection of the natural signal. It is to be noted that the Cl₂ pulse is generated on all occasions, and FF1 is reset for the refractory period following both oscillator reset and delivered stimulus pulses, such that incoming signals are blocked for the given refractory period following both events.

In the preferred embodiment, the pacer of this invention is characterized by the following specifications, which it is understood are exemplary and are subject to design choice modification:

TABLE I

Pulse interval: 860 ms
Pulse Width: 1 ms
Pulse Amplitude: limited to 10 ma
Extension of Pulse Interval when supply voltage falls approximately 25%: 50–60 ms
Extension of Pulse Width when supply voltage falls approximately 25%: 0.2 ms
Refractory Time: 340–360 ms
Interference Interval: 75 ms
Threshold of Received Signals: 1.5–2.0 mV
Current Drain: about 3 $\mu$A, unloaded The above characteristics, and in particular the low current drain, are achieved by the novel arrangement as shown in the preferred embodiment, without sacrifice of performance of the multiple functions desired of a demand pacer. The amplifier section provides a threshold detection function and, with the constant current source input circuits, operates with an extremely low current drain. The interface between the amplifier and logic sections enables extremely high signal gain and extremely low current drain, due to the fact that the OTA outputs are connected directly to high input impedance CMOS transistors, which in turn drive into a current source. By connecting a current source directly to both the CMOS outputs, very high gain operation is achieved which results in fast switching under current-limited operations.

In addition, it is to be noted that the amplifier, logic and oscillator portions are modularized, in that that the amplifier or oscillator designs can be changed and still interface with the logic circuitry. The logic portion, as well, can be changed subject to the limitations that the four paths between the logic portion and the oscillator be maintained.

Some of the more specific advantages of the pacer apparatus of this invention are to be noted. The FET current sources make extremely low currents possible, and are easy to adjust through setting of the source resistors. While specific configurations of current sources have been illustrated, other current source configurations in combination with the OTAs are within the scope of this invention as claimed. The OTAs may be utilized under very low current drain operation typically about 0.3 $\mu$A or less, including the bias current.

Note also that the employment of current sources as shown in FIG. 2 renders the adjustment of positive and negative amplifier sensitivity independent of each other, as well as independent of supply voltage. After trimming, the amplifier circuit may be used with different supply voltages without any appreciable change of sensitivity or current drain. While the embodiment illustrated provides for symmetrical positive and negative amplifier/comparator paths, if desired the sensitivities of the paths may be adjusted to be asymmetrical. Any offset voltages of the OTAs are compensated with the adjustment of the amplifier sensitivity.

It is also to be noted that the on-time of the two one shots is made substantially independent of supply voltage variations, due to the current source connections. The on-time of the one shots is determined by the time needed to charge capacitors 96 and 97 respectively to the threshold voltage of the MOS-FETS, which is about 1.5V for the circuit of FIG. 2. Without utilization of the current source configuration, resistors having on the order of about 25 Megohms would be required to achieve such independence, and such resistances would be unreliable and difficult to adjust. Further, the switching characteristics of the one-shots is also independent of supply voltage, e.g., for one-shot 55 the switching point is about 1.4 volts, the $V_P$ of the MOS-FETs.

I claim:

1. Low current drain apparatus for high gain signal amplification, comprising:

a. transconductance amplifier means for amplifying a received input signal, said amplifier means being characterized by having the circuit characteristic of a current source at its output, said current source being a function of the voltage level of said input signal;

b. an active circuit having an input and an output, said input being directly connected to the output of said transconductance amplifier means, said active circuit being characterized by having a high input impedance and being adapted to be driven at its output to a high or low state as a function of the signal at its input;

c. a current source circuit connected to said active circuit output; and d. a high input impedance load connected to said current source circuit and to said active circuit output.

2. The apparatus as described in claim 1, wherein said amplifier means comprises at least one operational transconductance amplifier having at least one input terminal and a bias current input terminal.

3. The apparatus as described in claim 2, wherein said active circuit comprises an integrated circuit transistor element.

4. The apparatus as described in claim 3, wherein said current source comprises a FET in combination with a resistance.

5. The apparatus as described in claim 4, comprising at least a second current source having its output connected to an input terminal of said at least one operational transconductance amplifier, said second current source being resistively connected to the bias current input terminal of said at least one operational transconductance amplifier.

6. The apparatus as described in claim 5, wherein said high input impedance load comprises a two state switchable circuit, said switchable circuit comprising a plurality of integrated circuit active elements.

7. The apparatus as described in claim 2, wherein said amplifier means comprises two operational transconductance amplifiers, and said active circuit comprises two integrated circuit transistor elements, said transistors having inputs connected to respective outputs of said amplifiers and having outputs connected commonly to said current source circuit.

8. The apparatus as described in claim 1, wherein said amplifier means comprises at least two operational transconductance amplifier units, a first circuit comprising a first current source connected to said first unit for maintaining said first unit as a low current drain amplifier, the output of said first unit being connected to an input of said second unit, and a second circuit comprising a second current source connected to said second unit and to the output of said first unit for maintaining operation of said second unit as a signal comparator.

9. The apparatus as described in claim 6, wherein said two state switchable circuit is a continuously settable one shot circuit.

10. Signal processing apparatus adapted for use in a system for providing physiological stimulus signals, comprising:

a. amplifier means for amplifying input signals from said physiological system, said amplifier means containing a plurality of transconductance amplifier devices;

b. a plurality of high input impedance active devices, each said active device having an input and an output, said active device inputs being connected to respective outputs of said transconductance amplifier devices; and c. current source means for providing at least one constant current source, said active device outputs being connected to said current source means.

11. The apparatus as described in claim 10, comprising a common connection at which said active device outputs are connected in common to said current source means.

12. The apparatus as described in claim 11, wherein said amplifier means comprises two operational transconductance amplifiers, and said plurality of active devices comprises two integrated circuit transistor elements connected to outputs of respective ones of said operational transconductance amplifiers.

13. The apparatus as described in claim 12, wherein said current source means comprises a single current source, the output of which is connected to said common connection.

14. The apparatus as described in claim 12, comprising second current source means connected to the inputs of said two output operational transconductance amplifiers, for maintaining the current drain of said two amplifiers.

15. Low current apparatus for signal amplification and processing, comprising:

a. amplifier means for amplifying a received input signal;

b. comparator means, having an input direct connected to an output of said amplifier means, for comparing said amplifier means output with a reference signal, said comparator means being characterized by having the circuit characteristic of a current source at its output, said current source output being a function of the level of said amplifier means output; and c. a high input impedance active device, said active device having an output and an input, said active device input being direct connected to the output of said comparator means, whereby said current source output characteristic and said high input impedance provide high gain signal amplification.

16. The apparatus as described in claim 15, comprising current source power supply means connected to said amplifier means, said comparator means, and said active device, said current source supply means acting to limit the total current drain of said apparatus.

17. The apparatus as described in claim 16, wherein said current source power supply means comprises a current source circuit connected to said active device output.

18. The apparatus as described in claim 16, wherein said amplifier means comprises an operational transconductance amplifier and said comparator means comprises an operational transconductance amplifier, each of said operational transconductance amplifiers having a bias current input terminal.

19. The apparatus as described in claim 18, wherein said current source supply means comprises means for connecting predetermined currents to the respective bias current input terminals of said operational transconductance amplifiers.

20. The apparatus as described in claim 19, wherein said current source supply means comprises sensitivity means for establishing the sensitivity of said amplifier means in combination with said comparator means.

21. The apparatus as described in claim 15, wherein said comparator means comprises two operational transconductance amplifier devices, and comprising connecting means for connecting respective inputs of said two operational transconductance amplifier devices to said amplifier means so that said two operational transconductance amplifier devices are oppositely driven.

* * * * *

UNITED STATES PATENT AND TRADEMARK OFFICE
CERTIFICATE OF CORRECTION

PATENT NO. : 4,097,766
DATED : June 27, 1978
INVENTOR(S) : Alexis C. M. Renirie

It is certified that error appears in the above-identified patent and that said Letters Patent are hereby corrected as shown below:

Column 9, line 22, delete "dafter" and insert --after--.

Column 10, line 20, before the comma, insert --and to the one-shot which is driven by the CMOS outputs--.

Signed and Sealed this

Thirteenth Day of March 1979

[SEAL]

Attest:

RUTH C. MASON
Attesting Officer

DONALD W. BANNER
Commissioner of Patents and Trademarks